US00RE34866E

United States Patent [19]

Kensey et al.

[11] E Patent Number: Re. 34,866

[45] **Reissued Date of Patent:* Feb. 21, 1995**

[54] DEVICE FOR SEALING PERCUTANEOUS PUNCTURE IN A VESSEL

[75] Inventors: Kenneth Kensey, Chester Springs; Harold E. Clupper, West Chester, both of Pa.

[73] Assignee: Kensey Nash Corporation, Exton, Pa.

[ * ] Notice: The portion of the term of this patent subsequent to Jan. 2, 2007 has been disclaimed.

[21] Appl. No.: 816,518

[22] Filed: Dec. 31, 1991

Related U.S. Patent Documents

Reissue of:

[64] Patent No.: 4,890,612
Issued: Jan. 2, 1990
Appl. No.: 194,641
Filed: May 16, 1988

U.S. Applications:

[63] Continuation-in-part of Ser. No. 15,267, Feb. 17, 1987, Pat. No. 4,744,364.

[51] Int. Cl.[6] ..... A61B 17/04
[52] U.S. Cl. ..... 606/213; 623/1
[58] Field of Search ..... 604/15, 60, 51, 285, 604/288; 128/831, 843, 865, 887, 897, 898, 899; 600/32; 623/1, 11; 606/213–218, 228–233

[56] References Cited

U.S. PATENT DOCUMENTS 1,191,736 7/1916 Roberson .
1,794,221 2/1931 Washburn .
2,386,590 10/1945 Calhoun ..... 604/15
3,675,639 7/1972 Cimber ..... 604/60
3,874,388 4/1975 King et al. .
4,007,743 2/1977 Blake .
4,031,569 6/1977 Jacob ..... 128/899
4,154,226 5/1979 Hennig et al. ..... 600/32
4,390,018 6/1983 Zukowski ..... 604/51
4,537,186 8/1985 Verschoof et al. .
4,587,969 5/1986 Gillis .
4,606,337 8/1986 Zimmermann et al. .
4,650,488 3/1987 Bays et al. ..... 128/899
4,710,192 12/1987 Liotta et al. .
4,744,364 5/1988 Kensey .
4,749,689 6/1988 Miyata et al. .

FOREIGN PATENT DOCUMENTS 0782814 11/1980 U.S.S.R. .

*Primary Examiner*—Ralph A. Lewis
*Attorney, Agent, or Firm*—Caesar, Rivise, Bernstein, Cohen & Pokotilow, Ltd.

[57] ABSTRACT

A device and method for sealing a puncture or incision formed percutaneously in tissue separating two internal portions of the body of a living being, e.g., a puncture or incision in an artery, in the gall bladder, in the liver, in the heart, etc. The device comprises plug means having a holding portion which is adapted to engage portions of the tissue adjacent the puncture or incision to hold the plug means in place and a sealing portion formed of a foam material and extending through the puncture or incision to engage the tissue contiguous therewith to seal the puncture or incision from the flow of body fluid therethrough. In the preferred embodiment, the closure or plug means is formed of a biodegradable material.

58 Claims, 4 Drawing Sheets

38
32

40
52
34
36
20
30
54
22
28
26
50
48
38
36
46
24
44

32
28
26
40
42
34
30

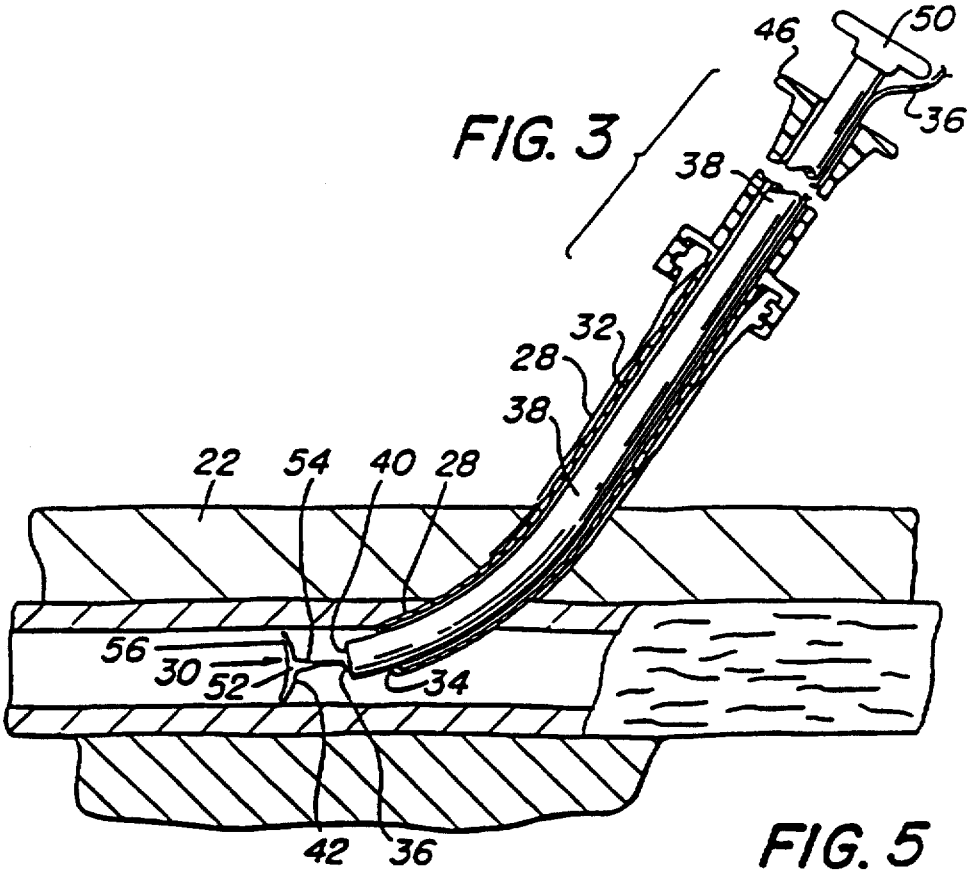
FIG. 3
FIG. 5
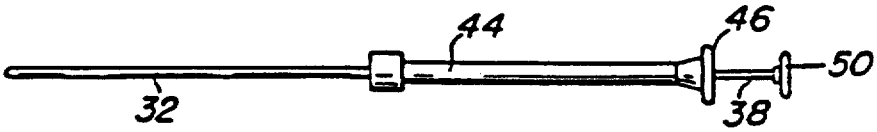
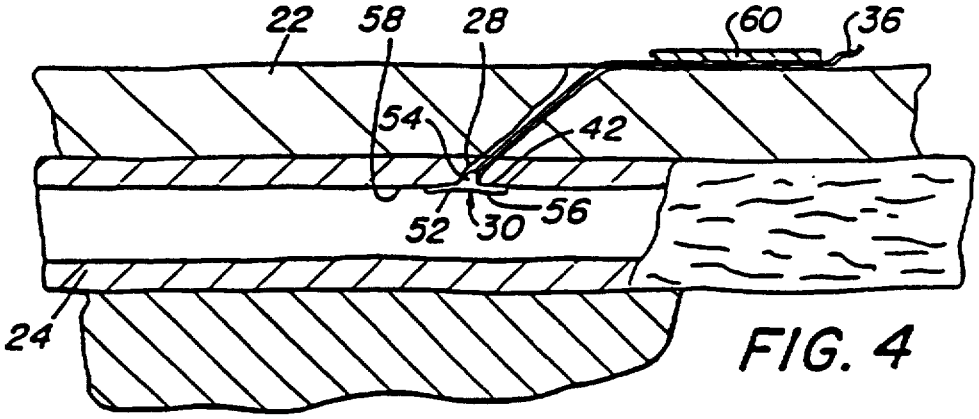
FIG. 4

FIG.6
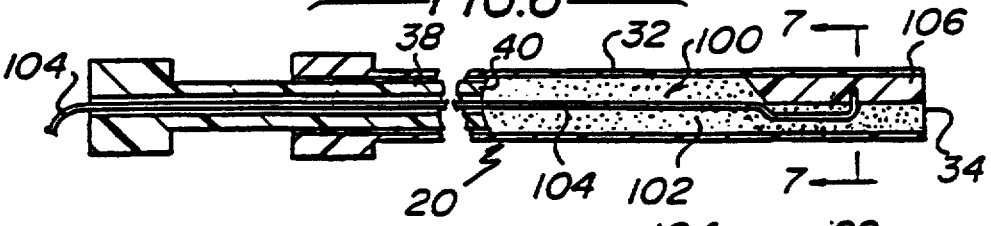
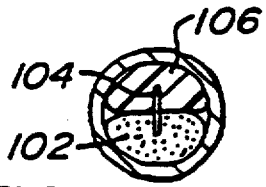
FIG.7
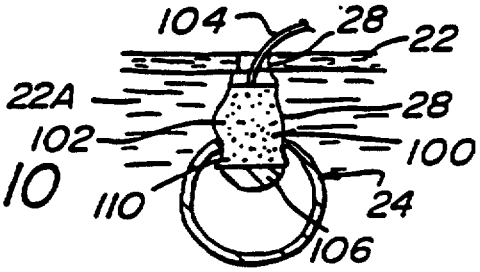
FIG.10
FIG.8
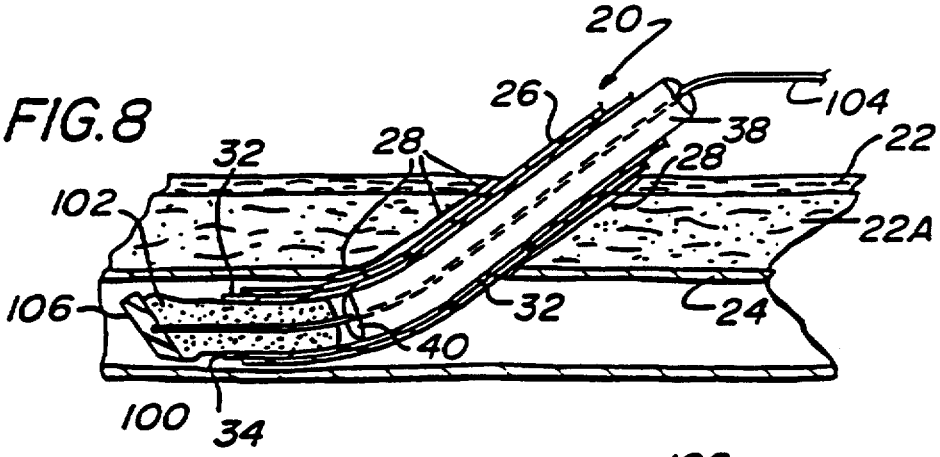
FIG.9
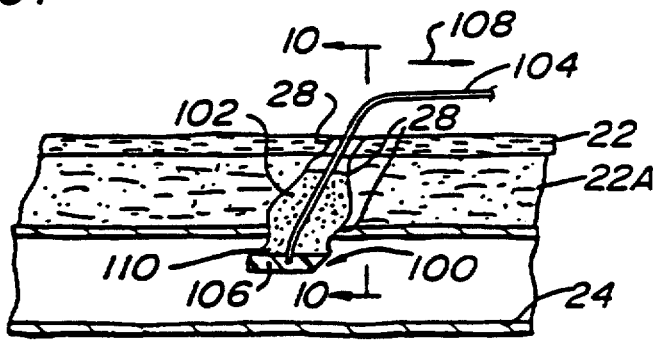

DEVICE FOR SEALING PERCUTANEOUS PUNCTURE IN A VESSEL

Matter enclosed in heavy brackets [ ] appears in the original patent but forms no part of this reissue specification; matter printed in italics indicates the additions made by reissue.

This invention relates generally to medical devices and more particularly to devices for sealing percutaneously formed punctures or incisions and is continuation-in-part of my copending U.S. patent application Ser. No. 07/015,267 filed on Feb. 17, 1987, now U.S. Pat. No. 4,744,364, entitled Device For Sealing Percutaneous Puncture In A Vessel, assigned to the same assignee as this invention and whose disclosure is incorporated by reference herein.

BACKGROUND OF THE INVENTION

As will be appreciated by those skilled in the art various surgical procedures are now being carried out intravascularly or intralumenally. For example in the treatment of vascular disease, such as atherosclerosis, it is a common practice to invade the artery to insert an instrument, e.g., a balloon or other type of catheter to carry out the procedure within the artery. Such procedures usually involve the percutaneous puncture of the artery so that in introducer sheath can be inserted into the artery and thereafter the instrument, e.g., catheter, itself can be inserted through the sheath to the operative position within the artery. Such procedures unavoidably present the problem of stopping the bleeding at the percutaneous puncture after the procedure has been completed and after the instrument (and any introducer sheaths used therewith) have been removed. At present such bleeding is stopped by the application of direct digital pressure over the puncture site by a trained physician or other suitably trained medical personnel. Such direct pressure has to be applied for a sufficiently long time for hemostasis to occurs that the opening is effectively closed against further bleeding. In the case of punctures into femoral or superficial femoral arteries the pressure may have to be applied for as long as forth-five minutes for hemostasis to occur. Not only is this direct digital pressure application procedure wasteful of time by highly skilled medical professionals, the procedure results in a substantial reduction, if not virtual arrest, of the flow of blood through the vessel. Since thrombosis is one of the major calamities that can occur in the immediate post operative period, any reduction in blood flow, such as caused by the application of digital pressure, is undesirable.

Applicator devices have been disclosed in the patent literature for inserting an absorbent plug or member into the vagina. Such devices basically comprises a tubular element adapted to be inserted into the vagina and having a plug of absorbent material located therein. The device also includes a plunger to push the plug out of the tubular element into the vagina. The plug also includes a thread or string attached to it to enable the plug to be retrieved from the vagina. Examples of such devices are shown in U.S. Pat. Nos. 1,191,736 (Roberson) and 1,794,221 (Washburn et al.).

While such devices are suitable for their intended purposes, there is no suggestion of their use, nor are they suitable for insertion into an opening in the wall of a blood vessel or other bodily lumen or duct to seal that opening.

The patent literature also includes devices for closing an opening in a blood vessel using sutures, see U.S. Pat. No. 4,587,909 (Gillis). Other means and techniques for closing a wound are disclosed in U.S. Pat. No. 4,606,337 (Zimmermann et al.).

None of the prior art teaches the use of simple means for effecting the closure of an opening, e.g., puncture, in the wall of a blood vessel, duct or lumen, by plugging the opening and without requiring sutures or the application of digital pressure.

A need also exists for devices and methods of sealing percutaneously formed punctures or incisions in other body tissues such as in the gall bladder, the liver, the heart, the lung, etc.

OBJECTS OF THE INVENTION

Accordingly, it is a general object of the instant invention to provide a device and methods of use which overcome the disadvantages of the prior art.

It is further object of the invention to provide a device and methods of use that is effective for closing off a puncture or other opening in a blood vessel, duct or lumen without the need for the application of digital pressure thereto and without resulting in any substantial reduction of blood flow through the vessel.

It is still a further object of the instant invention to provide an instrument which is simple in construction and whose method of use entails the ready insertion into a blood vessel, duct or lumen to position a closure therein for hemostatically sealing the puncture and without substantially blocking the flow of fluid through the vessel, duct or lumen.

It is yet a further object of the invention to provide a device and method of use for sealing percutaneously formed punctures or incisions in tissue separating two portions of the body of a living being from the flow of a body fluid therebetween.

SUMMARY OF THE INVENTION

These and other objects of the instant invention are achieved by providing a device and method for sealing a puncture or incision formed percutaneously in tissue separating two internal portions of the body of a living being, such as punctures or incisions in blood vessels, ducts or lumens, gall bladders, livers, hearts, etc. The device comprises a tubular body having an outlet at the distal end thereof and which is adapted to be inserted through the puncture or incision to expel a closure therefrom. The closure comprises a first holding portion adapted to engage portions of the tissue adjacent the puncture or incision to hold the closure in place and a second sealing portion formed of a foam material which is adapted to extend through the puncture or incision to engage the tissue contiguous with the puncture or incision to seal it from the flow of a body fluid therethrough between the two body portions.

BRIEF DESCRIPTION OF THE DRAWING

FIG. 3 is a side elevational view of the device 20 during the expulsion of its puncture sealing closure into the artery;

FIG. 4 is a side elevational view of the artery showing the sealing closure in place to close off the percutaneous puncture;

FIG. 5 is a reduced plan view of the device 20 of the subject invention;

FIG. 6 is a side elevational view of the device shown in FIG. 1 but including an alternative embodiment of the closure;

FIG. 7 is a sectional view taken along line 7—7 of FIG. 6;

FIG. 8 is a side elevational view of the embodiment of the device shown in FIG. 6 during the expulsion of its puncture sealing closure into an artery;

FIG. 9 is a side elevational view similar to that of FIG. 8 but showing the puncture sealing device in place within the puncture in the artery;

FIG. 10 is a sectional view taken along line 10—10 of FIG. 9;

DESCRIPTION OF THE PREFERRED EMBODIMENT OF THE INVENTION

Figures 1, 2:
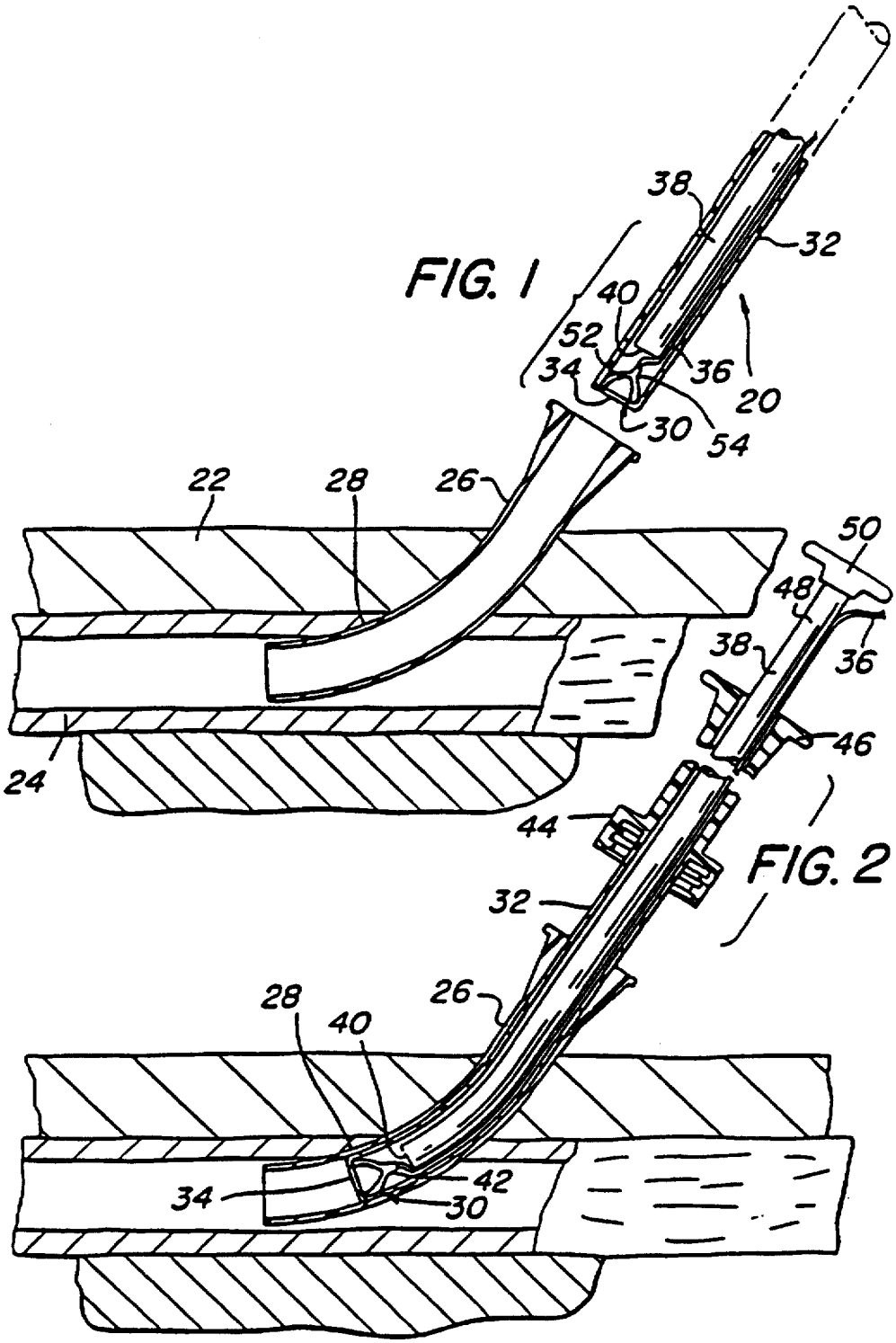
FIG. 1 is a side elevational view partially in section showing a portion of one device constructed in accordance with this invention about to be inserted into a conventional sheath extending through a percutaneous puncture into an artery.
FIG. 2 is a side elevational view of the device 20 in place in the sheath.

Referring now in greater detail to the various figures of the drawing wherein like reference characters refer to like parts, there is shown generally at 20 in FIG. 1 an instrument for effecting the closure of a puncture or other opening in a blood vessel, duct or lumen in a living being. The device 20 thus has particular utility when used in connection with intravascular procedures, such as angiographic dye injection, balloon angioplasty and other types of recanalization of atherosclerotic arteries, in-situ valvulectomy, etc. However, it should be appreciated that the device 20 can be used to hemostatically close a puncture or other opening in othe types of duct or lumens within the body. Thus, it is to be understood that while the description of the invention as contained herein is directed to closing off percutaneous punctures in arteries, the device 20 has much more wide-spread applications.

Before describing the instrument 20 itself a brief description of a typical, conventional, intravascular surgical procedure, e.g., catheter instrumentation of an artery, utilizing a percutaneous incision or puncture will be given to best appreciate the features of the device 20. In such a procedure a cannula of an instrument, such as an angiogrpahic needle (not shown), is inserted percutaneously through the skin into the artery, such as the femoral artery 24 at the situs for the instrument's insertion. The needle cannula is held in place and the flexible end of a mini-guidewire (not shown) is then passed through the cannula into the artery to the desired depth (i.e., longitudinal position therealong). Once the mini-guidewire is in place the needle cannula is removed leaving the guidewire in place. A conventional introducer sheath 26 and an arterial dilator (not shown) are then passed over the guidewire through the puncture 28 and into the artery 24. The guidewire and then the dilator are removed leaving the sheath 26 in place. The catheter (not shown) or other intravascular instrument (not shown) is then inserted through the introducer sheath 24 and threaded down the artery to the desired intravascular location, e.g., the situs of an atherosclerotic occlusion. Once the intravascular procedure (e.g., angioplasty) has been completed the catheter is removed. Thereafter the sheath is removed and the surgeon or other trained person applies digital pressure to the percutaneous puncture until hemostasis has occurred.

The device 20 effects the hemostatic closure of a percutaneous or other type of puncture, incision or opening in an artery or other body duct or lumen without necessitating the application of pressure thereto. Thus, once the catheter or other intravascular instrument has been removed but with the sheath 26 left in place, the device 20 of the subject invention is inserted through the sheath 26 into the artery 24 and operated to expel a closure member 30 (to be described later) into the artery. The closure is arranged to be drawn back into the puncture 28 to seal it. The sheath is removed and the closure left in place. Due to its construction the closure is ultimately absorbed by the surrounding tissue.

As can be seen in FIG. 1 the device 20 basically comprises a tubular body 32 having an outlet 34 at its distal end, the heretofore identified closure member 30 having a retraction filament 36 connected thereto, and pusher means 38. The tubular body is an elongate member preferably constructed of a sufficiently small outside diameter, e.g., 8 F (French), and somewhat flexible material, such as polyethylene or polyvinylchloride, to enable it to be inserted through the introducer sheath 26 into the artery 24, with the tubular body's outlet 34 within the artery distally of the puncture 28.

The closure member 30 is an expandable member which, when contracted or compressed is sufficiently compact to fit within the interior of the tubular body 30, but when unconstrained by the tubular body it expands to an enlarged configuration (See FIGS. 3 and 4) suitable for closing off the puncture 28 in the artery. Thus, closure member 30 is formed by a resilient, hemostatic material, which is preferably biodegradable, so that it need not be removed after placement. One particular effective material is a porous hemostatic absorbable gelatin sold by Johnson & Johnson, Inc. under the name Gelfoam.

The pusher means 38 basically comprises an elongated, cylindrical rod-like member, having a distal end 40. The pusher is also formed of a relatively flexible material, such as polyethylene or polyvinylchloride and is disposed within the interior of tubular body 32. The outside diameter of the pusher is slightly less than the inside diameter of the tubular body portion to enable the pusher to be manually moved (slid) down the longitudinal axis of the body portion 28, to push or force the closure 30 out of the outlet 34. Thus the pusher is arranged to be moved from a retracted position, like that shown in FIG. 2 to an extended position like that shown in FIG. 3 wherein its distal end 40 is located close to the outlet 34 of the body 32. When the pusher is moved to the extended position its distal end forces the closure member 30 out of the outlet 34.

The heretofore identified retraction filament 36 constitutes an elongated thread, preferably formed of a long, yet very thin, biodegradable material, such as an absorbable suture, and is fixedly secured to the proximal side 42 of the closure member 30 at the middle thereof. When the closure is in position within the tubular body the thread 36 extends down the length of the tubular body 32 between it and the pusher 38 so that the proximal end of the thread is located outside the device 20.

The thread 36 being long and thin does not interfere with the operation of the pusher expelling the closure member 32 out of outlet 34. Thus, during the expulsion of the closure into the artery the thread 36 slides down the tubular member with the closure. The thread 36 is sufficiently long that a substantial length extends outside of the proximal end of the device 20 even after the closure is in the artery.

In order to effecuate the movement of the pusher from the retracted to the extended position the tubular body includes a collar 44 having a flanged projection 46 arranged to be grasped by the fingers of the user of the device 20. In addition the proximal end 48 of the pusher 38 includes an enlarged cap 50 arranged to be engaged by the user's thumb. Thus, to effect the ejection of the closure member 30 all the user of the device 20 merely has to do is to grasp the projection 46 with his/her fingers while applying pressure to the cap 50 with his/her thumb. This action forces the pusher down the tubular body to the extended position.

As can be seen in FIGS. 3 and 4, when the closure member 30 is in its unconstrained state (such as when it is ejected into the artery) it assumes a configuration having an enlarged head portion 52 and an anchor portion 54. The head portion is of generally disk-like shape of relatively large diameter, e.g., 6–9 mm, yet relatively thin, e.g. 1–2mm. The head portion includes the rear (proximal) surface 42 and a front (distal) surface 56. The anchor portion 54 consists of a small diameter, e.g., 2–3 mm, hub-like projection from the proximal surface 50 at approximately the center thereof. The distal end of the retraction thread 36 is fixedly secured to the anchor portion 54. The resilient nature of the closure enables the enlarged head portion 52 to conform to the surface 58 of the interior of the artery 24 contiguous with the puncture 28 so that its proximal surface 42 intimately engages the artery surface 58 while the hub-like anchor portion 54 extends somewhat into the puncture 28 to hemostatically seal the puncture when the closure is pulled into place, as will be described hereinafter.

Thus, as shown in FIG. 3, after the tubular body 32 of device 20 has been inserted into the sheath 26 so that its outlet 34 is within the artery, the sheath 26 is withdrawn. The pusher is then extended or pushed down the tubular body as described heretofore so that its distal end portion 40 forces the closure 30 out of outlet 34. Once the closure 30 is outside the confines of the tubular body 32 it expands or enlarges to its disk-shaped configuration. After the closure is pushed out of the tubular member by the pusher, the tubular body is itself withdrawn from the puncture 28 in the artery and moved completely outside the body of the patient. This action leaves the closure 30 within the artery and with the retraction filament extending through the puncture 28 so that a substantially portion of the filament is outside the patient's body. The filament is then pulled by its proximal end to cause the closure to move toward the puncture 28, until its anchor portion 42 is somewhat within the puncture and its engagement surface 50 is in intimate engagement with the interior of the artery wall contiguous with the puncture. This action hemostatically seals the puncture. In order to hold the closure in place the thread 34 is held taut and is secured in position on the patients skin, such as by use of a strip of conventional tape 60. Alternatively, some other gripping means (not shown) can be used to slide down the filament into contact with the skin while together gripping the filament tightly to prevent it from slipping.

By virtue of the fact that the head portion 52 of the closure is thin and conforms to the interior surface of the artery, it does not block off or otherwise impede the flow of blood through the artery.

It should be noted at this juncture that the closure can be of any suitable shape and need not be of the disk-like shape shown herein, so long as once it is pulled into position at the situs of the puncture it serves to hemostatically seal that puncture without appreciably blocking the passageway. Moreover, in order to minimize the risks of thrombosis in the artery the front (distal) face 56 of the closure 30, which is exposed to the flow of blood through the artery, may be coated with a non-thrombogenic material. This feature serves to minimize the risk of thrombosis forming in the artery. The thrombogenic material used can comprise a waxy coating, such as coconut oil, on the closure's front surface 56.

As mentioned earlier the closure and its retraction filament are each preferably formed of an absorbable (e.g., biodegradable) material. This feature enables the closure to be left in place after hemostatis has occurred since it will be absorbed by the bodily tissues thereafter. Accordingly, the closure does not have to be removed after having served its purpose.

In order to accellerate hemostasis the nature forming the closures of the invention may include conventional clotting agents, such as tissue throboplastin.

In FIG. 6 there is shown an alternative embodiment of the closure utilized in a device 20 for sealing a percutaneous puncture or incision. The alternative embodiment of the closure is designated by the reference numeral 100 and basically comprises three components, namely, a holding member [102] *106*, a suture or filament 104, and a sealing member [106] *102*. The holding member is an elongated body constructed like a toggle and is preferably formed of a biodegradable, thermoplastic polymer, such as polyglactide. This material will degrade within the body within a short period of time, e.g., approximately 45 days. The toggle is molded onto the distal end of the filament 104 which is slightly bulbous to hold the toggle in place thereon. The filament is also preferably formed of polyglactide (e.g., it will degrade within the body in approximately 90 days). The filament is quite flexible so that the toggle can pivot to various orientations with respect to it. Disposed promixally behind the toggle is the sealing member [106] *102*. That member basically comprises a cylindrical plug preferably formed of a compressed foam which is highly absorbent and which, when disposed within the body, swells in excess of its compressed diameter, e.g., swells to twice its compressed diameter. The plug is preferably formed of gelatin or collagen foam so that it also degrades quickly within the body, e.g., in approximately ten days or so. The filament extends fully through the plug.

The closure 100 is located within the device 20 adjacent the outlet 34 of the tubular portion 32 thereof. In particular, the foam plug or sealing portion 102 is located immediately adjacent the free end 40 of the plunger 38, with the toggle or holding portion 106 located at the distal end of the portion 102. The toggle is oriented so that its longitudinal axis is parallel to the longitudinal axis of the device 20. When so disposed the toggle compresses a portion of the distal end of the plug portion. The filament 104 extends backward from the toggle portion through the plug portion and through a central passageway in the plunger 38 to a point outside the device 20. The closure is introduced into the artery, or into a puncture or incision in any body tissue, such as the liver (FIG. 11), gall bladder (FIG. 11), lung (FIG. 12), heart (FIG. 12), etc., until the insertion device's outlet 34 is in the desired position.

In the case of the sealing of an artery, the outlet 34 of the device is positioned so that it is within the artery (See FIG. 8) and just slightly beyond the introducer sleeve 26. This placement is controlled by stops (not shown) on the device 25. The plunger 38 is then operated as described earlier to expel the closure 100. Once the closure is expelled, the device 20 is held in this position for a short period of time, e.g., 15 to 60 seconds, to allow the foam at the tip of the closure, i.e., the distal end of portion 102, to swell. This action effectively tips the toggle. The insertion device 20 is then removed in a similar manner as described earlier and the closure's filament 104 then retracted, that is, pulled in the direction of arrow 108 in FIG. 8. This action pulls the closure's plug portion 102 back through the puncture or incision 28 in the artery wall until its toggle portion 106 engages the inner surface of the arterial wall to stop further retraction. As the toggle comes into engagement with the arterial wall, it effects the compression of the distal end portion 110 of the plug portion 102. Moreover, the proximal end portion of the plug 102 extends into the puncture or incision in the subcutaneous tissue 22A to a point closely adjacent the skin 22. These actions effectively seal the puncture or incision from the passage of blood therethrough.

It should be noted that the engagement of the toggle with the inner surface of the artery wall can either be direct or indirect, the latter being through the interposed deformed distal end portion of the plug 102. In either event, the toggle serves to act as a stop precluding the closure 100 from being pulled out of sealing engagement with the puncture or incision 28.

In lieu of the use of the toggle/foam plug closure 100, one can utilize an alternative closure 200. The closure 200 basically comprises a preformed foam plug having an enlarged distal end portion 106 (See FIGS. 11 and 12) serving as the heretofore described holding member, a proximally located rod-like portion 102 (See FIGS. 11 and 12) serving as the heretofore described sealing member and a retraction filament 104 secured thereto. The closure 200 is preferably formed of a dense collagen foam with long collagen fiber reinforcement so that it has a high expansion ratio (wet-to-dry) and good mechanical wet strength.

The closure 200, like closures 30 and 100 is held within the tubular portion 32 of the insertion device 20 in a compressed state and with its holding portion 106 located immediately adjacent the outlet 34. For sealing punctures or incisions in arteries the device 20 is introduced into the artery in the manner as described heretofore. The pusher member 38 then pushes the foam closure out of the outlet, whereupon the holding portion 206 swells upon contact with the blood in the artery. The insertion device 20 is then removed so that the closure 200, now swollen, hangs up at the puncture or incision 28 within the arterial wall, i.e., the enlarged holding member portion 206 engages the inner surface of the arterial wall and the sealing portion 102 extends fully through the puncture or incision into the subcutaneous tissue 22A. The retraction of the filament fully seats the closure in place so that the sealing portion extends fully through the puncture or incision in the artery wall and with its proximal end located within the subcutaneous tissue closely adjacent the skin.

The advantage of the preformed foam closure as just described over the toggle/plug closure 100 is that it is considerably simpler in construction, assembly and cost.

Figure 11:
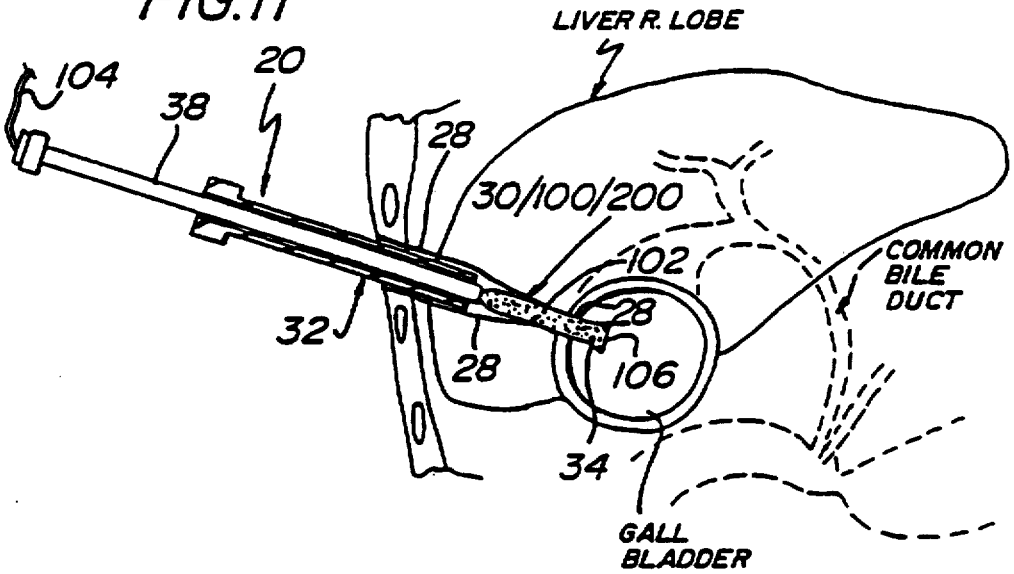
FIG. 11 is a sectional view through the body of the being showing the sealing of a percutaneous incision or puncture in the gall bladder and liver.

As mentioned earlier, it is frequently desirable to be able to seal a puncture or incision in body organs or tissue other than blood vessels. For example, in cases where percutaneous transhepatic punctures are made into the gall bladder for purposes of introducing chemicals or mechanical instruments, there exists a very real risk of bile leakage into the peritoneum via the liver puncture site, thereby resulting in a dangerous possibility of peritonitis. The closures 30, 100 and 200, as described heretofore, can be utilized to seal such percutaneous punctures or incisions to eliminate the risks of bile leakage. For example, as shown in FIG. 11 an insertion device 20 with a closure 100 to 200 disposed therein is introduced through the puncture or incision 28 in the right lobe of the liver and through the puncture or incision in the gall bladder so that the devices outlet 34 extends just beyond its introducer sheath 26. The plunger 38 is then pressed to eject the closure so that the holding portion 106 thereof is located within the gall bladder and in engagement with the inner surface thereof, while the sealing portion 102 extends through the puncture or incision in the gall bladder and into the puncture or incision in the liver. Alternatively, the closure 100/200 may be left in the incision or puncture 28 in the liver alone, if that makes best sense from a medical/surgical standpoint.

Figure 12:
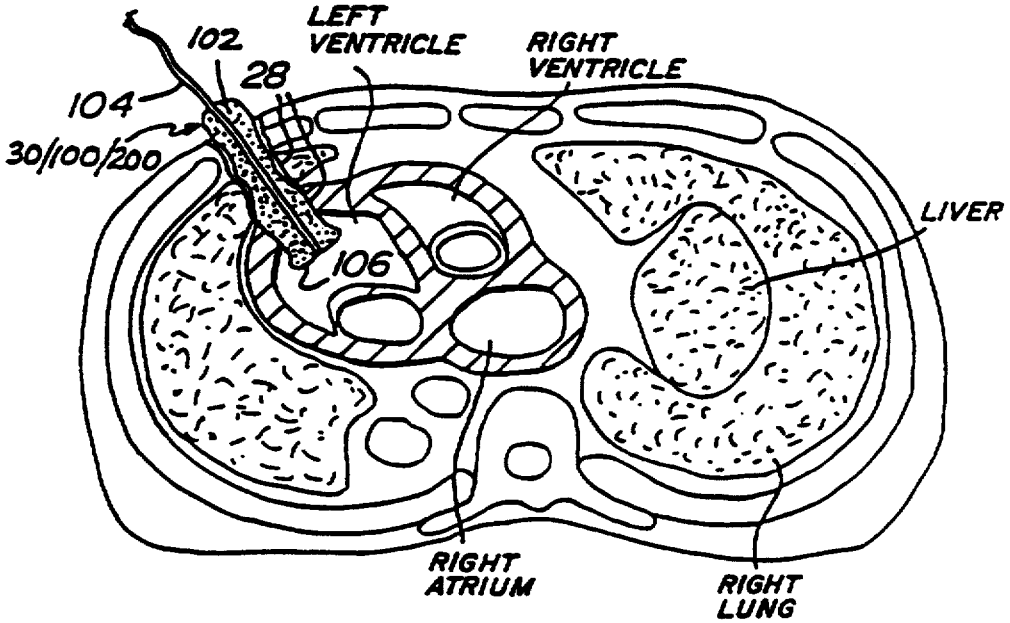
FIG. 12 is a sectional view through the body of the being showing the sealing of a wound in the lung and heart.

The subject invention is also useful for effecting the sealing of percutaneous incisions or punctures in the heart, such as could result from a wound. In this connection, as shown in FIG. 12, a wound penetrating the left lung and left ventricle may be sealed by introducing the insertion device 20 with a closure 100/200 therein through the wound, through the puncture in the lung, and into the puncture in the left ventricle. The closure 100/200 is then ejected so that its holding portion 106 is located within the ventricle, while its sealing portion 102 extends through the puncture in the left ventricle wall and through the puncture in the left lung. In such applications, it is preferred that the closure member 100/200 be configured so that its sealing portion 102 is of a substantial length to extend not only through the puncture in the left ventricle, but also the puncture in the lung and through the wound in the skin to some exterior point closely adjacent the skin. Thus, the closure 100/200 acts as a tamponade.

As should be appreciated by those skilled in the art, the device and methods of this invention as well as the closure device mentioned in my copending U.S. patent application, can be utilized to seal a percutaneous incision or puncture in any body tissue or organ to prevent the flow of fluid through that puncture or incision from one body portion to another.

Without further elaboration the foregoing will so fully illustrate by invention that other may, by applying current or future knowledge, adopt the same for use under various conditions of service.

What is claimed is:

1. A closure device for sealing a puncture or incision formed percutaneously in tissue separating two internal portions of the body of a living being, *said tissue having an inside and an outside portion, said puncture or incision including a first portion extending through said tissue from said inside portion to said outside portion and a second*

*portion extending from said first portion of said puncture or incision to the surface of said skin,* said device comprising plug means arranged for placement at a predetermined position within the body of said being and having a first holding portion and a second sealing portion [adapted], *said first holding portion being preformed in a predetermined shape and being orientable into a first orientation to enable it to be extended in a first direction through said incision or puncture and thereafter orientable into a second and different orientation without changing from said predetermined shape so that it can be retracted in a second direction opposite to said first direction* to [engage] *a position contiguous with the inside* portions of the tissue adjacent said puncture or incision *without being pulled through said puncture or incision* to hold said plug means in place, *said second sealing portion being configured for location within said second portion of said puncture or incision, and being* formed of an expandable material which expands automatically in response to the ambient surroundings when in said [predetermined position and extending through said] *second portion of* said puncture or incision to engage [the] tissue contiguous therewith to seal said puncture or incision from the flow of a body fluid therethrough [between said two internal portions].

2. The device of claim 1, wherein said expandable material comprises a collagen foam.

3. The device of claim 1, wherein said expandable material comprises a gelatinous foam.

4. The device of claim 1 wherein said tissue comprises *the wall of* a blood vessel and wherein said second sealing portion *is shaped to* extend[s fully] through said *second portion of said* puncture or incision [in the wall of said blood vessel] to a point adjacent the skin of the being.

5. The device of claim 4 wherein said expandable material comprises a collagen foam.

6. The device of claim 4 wherein said expandable material comprises a gelatinous foam.

[7. The device of claim 1 wherein said tissue comprises the gall bladder and wherein said second sealing portion extends fully through said puncture or incision in the wall of said gall bladder and into a cooperating puncture or incision in the liver of said being.]

[8. The device of claim 7, wherein said expandable material comprises a collagen foam.]

[9. The device of claim 7, wherein expandable material comprises a gelatinous foam.]

[10. The device of claim 1 wherein said tissue comprises the liver of said being and wherein said second sealing portion extends substantially into said puncture or incision in said liver.]

[11. The device of claim 10 wherein said expandable material comprises a collagen foam.]

[12. The device of claim 10 wherein said expandable material comprises a gelatinous foam.]

[13. The device of claim 1 wherein said tissue is the heart of said being and wherein said second sealing portion extends through said incision or puncture in said heart to a point closely adjacent the skin of said being.]

[14. The device of claim 13 wherein said expandable material comprises a collagen foam.]

[15. The device of claim 13 wherein said expandable material comprises a gelatinous foam.]

16. The device of claim 1 additionally comprising retraction means.

17. The device of claim 16 wherein said retraction means comprises a filament secured to said holding portion.

18. The device of claim 17 wherein said holding portion toggles with respect to the sealing portion.

19. The device of claim 18 wherein said filament and said [toggle] *holding portion* are each formed of a biodegradable material.

[20. The device of claim 1 wherein said tissue is a lung of said being and wherein said second sealing portion extends through said incision or puncture into said lung to a point closely adjacent the skin of said being.]

[21. The device of claim 20 wherein said expandable material comprises a collagen foam.]

[22. The device of claim 20 wherein said expandable material comprises a gelatinous foam.]

23. The method of sealing a small puncture or incision formed percutaneously in tissue separating two internal portions of the body of a living being by the use of plug means, *said tissue having an inside portion and an outside portion, said puncture or incision including a first portion extending through said tissue from said inside portion to said outside portion and a second portion extending from said first portion of said puncture or incision to the surface of said skin, said plug means* comprising a first holding portion and a second sealing portion, *said first holding portion being preformed in a predetermined shape, said second sealing portion being* formed of an expandable material which expands automatically in response to the ambient surroundings when in the body of said being, said method comprising *orienting said first holding portion into a first orientation without changing said predetermined shape, inserting said first holding portion while in said first orientation* [inserting said plug means] percutaneously into said puncture or incision *in a first direction, orienting said first holding portion into a second orientation without changing said predetermined shape and retracting said first holding portion while in said second orientation in a second, opposite direction to said first direction* so that said first holding portion [engages] *is pulled into a position contiguous with inside* portions of said tissue *adjacent said puncture or incision and without being pulled through said puncture or incision* to hold said plug means in place and with said second sealing portion extending through said puncture or incision [expanding] *so that said sealing portion is located within said second portion of said puncture or incision, whereupon said second portion expands automatically to engage* [the] tissue contiguous therewith to seal said puncture or incision from the flow of a body fluid therethrough [between said two internal portions].

24. The method of claim 23 wherein said tissue comprises *the wall of* a blood vessel and wherein said second sealing portion is [arranged] *shaped* so that its extends [fully] through said *second portion of said* puncture or incision [in the wall of said blood vessel] to a point adjacent the skin of the being.

25. The method of claim 24 wherein said expandable material comporises of a collagen foam.

26. The method of claim 24 wherein said expandable material comprises a gelatinous foam.

27. The method of sealing a small puncture or incision formed percutaneously in the gall bladder by use of plug means comprising a first holding portion and a second sealing portion formed of an expandable material, said method comprising inserting said plug means percutaneously into said puncture or incision so that said first holding portion engages portion of said gall bladder to hold said plug means in place and with said second sealing portion extending fully through said puncture or incision in the wall of said gall bladder and into a cooperating puncture or incision in the liver of said being to seal said puncture or incision from the flow of a body fluid therethrough.

28. The method of claim 27 wherein said expandable material comprises a collagen foam.

29. The method of claim 27 wherein said expandable material comprises a gelatinous foam.

30. The method of claim 27 wherein said second sealing portion automatically expands in response to the ambient surroundings when in the body of said being in said puncture or incision.

31. The method of sealing a small puncture or incision formed percutaneously in the liver of a living being by the use of plug means comprising a first holding portion and a second sealing portion formed of an expandable material, said method comprising inserting said plug means percutaneously into said puncture or incision so that said first holding portion engages portions of said liver to hold said plug means in place and with said second sealing portion extending substantially into said puncture or incision in said liver to engage the tissue contiguous therewith to seal said puncture or incision from the flow of body fluid therethrough.

32. The method of claim 31 wherein said expandable material comprises a collagen foam.

33. The method of claim 31 wherein said expandable material comprises a gelatinous foam.

34. The method of claim 31 wherein said second sealing portion automatically expands in response to the ambient surroundings when in the body of said being in said puncture or incision.

35. The method of sealing a small puncture or incision formed percutaneously in the heart of a living being by use of plug means comprising a first holding portion and a second sealing portion formed of an expandable material, said method comprising inserting said plug means percutaneously into said puncture or incision so that first holding portion engages portions of said heart to hold said plug means in place and with said second sealing portion extending through said incision or puncture in said heart to a point closely adjacent the skin of said being and engaging the tissue contiguous therewith to said seal puncture or incision from the flow of body fluid therethrough.

36. The method of claim 35 wherein said expandable material comprises a collagen foam.

37. The method of claim 37 wherein said expandable material comprises a gelatinous foam.

38. The method of claim 35 wherein said second sealing portion automatically expands in response to the ambient surroundings when in the body of said being in said puncture or incision.

39. The method of sealing a small puncture or incision formed percutaneously in a lung of a living being by the use of plug means comprising a first holding portion and a second sealing portion formed of an expandable material, said method comprising inserting said plug means percutaneously into said puncture or incision so that said first holding portion engages portion of said lung to hold said plug means in place and with said second sealing portion extending fully through said puncture or incision in said lung to a point closely adjacent the skin of said being to engage the tissue contiguous therewith to seal said puncture or incision from the flow of a body fluid therethrough.

40. The method of claim 39 wherein said expandable material comprises a collagen foam.

41. The method of claim 39 wherein said expandable material comprises a gelatinous foam.

42. The method of claim 39 wherein said second sealing portion automatically expands in response to the ambient surroundings when in the body of said being in said puncture or incision.

*43. A method of sealing a small puncture or incision formed percutaneously in a blood vessel of the body of a living being by use of a plug means comprising first and second portions, said first portion being positioned distally of said second portion in use, at least one of said portions being formed of an expandable material, a flexible retraction means being operatively connected to said first portion of the plug means and extending beyond the being's skin after the plug means has been inserted percutaneously into said puncture or incision, said method comprising the steps of: inserting said plug means percutaneously into said puncture or incision; maneuvering said flexible retraction means from a location beyond the being's skin for adjusting the plug means after it has been inserted so that said plug means is in an orientation wherein said first portion is located within said blood vessel to act as a stop to prevent retraction of said plug means out of said puncture or incision and wherein said second portion engages a portion of the being's body located between the exterior surface of the blood vessel and the surface of the being's skin, said first and second portions cooperating for sealing said puncture or incision from the flow of blood passing through said blood vessel.*

*44. The method of claim 43, including the step of forming said second portion of said expandable material for expanding into engagement with portions of the being's body located between the exterior surface of the blood vessel and the surface of the being's skin.*

*45. The method of claim 44 wherein said expansion of said second portion occurs automatically in response to the presence of blood.*

*46. The method of claim 44 wherein said second portion promotes hemostasis and aids in holding said plug means in position for sealing the puncture or incision.*

*47. The method of claim 43, including the step of forming said first and second portions of said plug means of materials which are absorbable within the body after a period of time sufficient for permitting effective closure of said incision or puncture.*

*48. The method of claim 47, including the step of selecting the materials of said first and second portions of said plug means for causing said second portion to be absorbed within the body in a shorter period of time than said first portion.*

*49. The method of claim 48 including the steps of forming said first portion and second portion of different materials.*

*50. The method of claim 43, including the step of forming said plug means and flexible retraction means of a material which is absorbable within the body after a period of time sufficient for permitting effective closure of said incision or puncture.*

*51. The method of claim 43, including the steps of performing said first portion, prior to use of the plug means, in a configuration for permitting insertion of the first portion through the puncture or incision of the blood vessel to a position within said blood vessel when the first portion is in a first orientation relative to said second portion, and for permitting the first portion to bridge the puncture or incision within said blood vessel when said first portion is in a*

*second orientation relative to said second portion for preventing the plug means from being pulled out of the blood vessel during the step of employing the retraction means to assist in locating the plug means for sealing the puncture or incision, and arranging said preformed first portion distally of said second portion in use for permitting said first portion to be positioned in the first orientation when the first portion is being inserted into the blood vessel through the puncture or incision, and then to be toggled relative to said second portion into said second orientation when in the interior of the blood vessel.*

*52. The method of claim 51 including the step of forming said second portion of said expandable material for expanding into engagement with internal body tissue after said first portion has been inserted into the interior of the blood vessel, said second portion being arranged relative to said first portion for aiding in toggling said first portion into said second orientation upon expansion of said second portion.*

*53. The method of claim 52 wherein said expansion of said second portion occurs automatically in response to the presence of blood.*

*54. The method of claim 43 wherein said second portion promotes hemostatis and aids in holding said plug means in position for sealing the puncture or incision.*

*55. The method of claim 43 including the step of operatively connecting the flexible retraction means to the first portion by connecting the retraction means to the first portion and in a location extending along said second portion.*

*56. The method of claim 55 including the step of positioning the retraction means through the second portion.*

*57. A plug device for sealing a small puncture or incision formed percutaneously in a wall of a blood vessel of a living being, said device comprising a plug including a first portion and a second portion, said first portion being positioned distally of said second portion in use, and said device further including a flexible retraction means operatively coupled to the plug for extending beyond the being's skin after the plug has been inserted percutaneously into said puncture or incision in the wall of the blood vessel, one of said first and second portions of said plug being formed of an expandable material, said plug being configured to be inserted percutaneously into said puncture or incision such that retraction of said retraction means causes said first portion of said plug to move to a position within said blood vessel to act as a stop to prevent the retraction of said plug out of said puncture and said second portion of said plug being in engagement with internal tissue portions of the being's body located between the exterior surface of the wall of said blood vessel and the surface of the being's skin when said plug is positioned in said puncture or incision, said second portion of said plug being movable into engagement with said internal tissue portions for aiding in holding said plug in a position for sealing said puncture or incision from the flow of blood therethrough.*

*58. The plug device of claim 57 wherein said second portion of the plug is formed of an expandable material and is expanded into engagement with said internal tissue portions to retain said plug in said position for sealing said puncture or incision from the flow of blood therethrough.*

*59. The plug device of claim 58 wherein said second portion of the plug comprises a material which expands automatically in response to the presence of blood.*

*60. The plug device of claim 59 wherein said second portion of the plug comprises a material which promotes hemostatis and aids in holding said plug device in said position.*

*61. The plug device of claim 58 wherein said second portion of the plug comprises a material which promotes hemostatis and aids in holding said plug device in said position.*

*62. The plug device of claim 57 wherein said first portion of said plug is configured to be positioned along the inner surface of the blood vessel to obstruct the flow of blood into the puncture or incision from the blood vessel.*

*63. The plug device of claim 57 wherein the flexible retraction means is directly connected to the first portion of the plug and extends along the second portion of the plug.*

*64. The plug device of claim 63 wherein the flexible retraction means extends along the second portion of the plug by extending through the second portion.*

*65. The plug device of claim 57 wherein said first and second portions of said plug are formed of materials which are absorbable within the body after a period of time sufficient for permitting effective closure of said incision or puncture.*

*66. The plug device of claim 65 wherein the second portion of the plug is absorbed within the body in a shorter period of time then said first portion.*

*67. The plug device of claim 66 wherein said first portion and said second portion of the plug are constructed of different materials.*

*68. The plug device of claim 57 wherein said first portion of the plug is preformed in a configuration for permitting insertion of the first portion through the puncture or incision of the blood vessel to a position within said blood vessel when the first portion is in a first orientation relative to the second portion of the plug, and for permitting said first portion to bridge the puncture or incision within said blood vessel when said first portion is in a second orientation relative to said second portion for preventing the plug from being pulled out of the blood vessel, said preformed first portion being located distally of the second portion in use of the plug device for permitting the first portion to be positioned in the first orientation when the first portion is inserted into the blood vessel through the puncture or incision and then to be toggled relative to said second portion into said second orientation when in the interior of the blood vessel.*

*69. The plug device of claim 68 wherein the second portion of the plug is formed of an expandable material, said expandable material being positioned relative to the first portion for causing movement of the first portion into the second orientation upon expansion of the second portion.*

*70. The plug device of claim 69 wherein the second portion of the plug comprises a material which expands automatically in response to the presence of blood.*

* * * * *